(12) United States Patent
Cise et al.

(10) Patent No.: US 11,191,566 B2
(45) Date of Patent: Dec. 7, 2021

(54) INTRODUCER WITH PARTIALLY ANNEALED REINFORCEMENT ELEMENT AND RELATED SYSTEMS AND METHODS

(71) Applicant: Merit Medical Systems, Inc., South Jordan, UT (US)

(72) Inventors: David Cise, Herriman, UT (US); Doug Hales, South Jordan, UT (US); Alex Singleton, Sandy, UT (US); Bryan Heaton, Kaysville, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 115 days.

(21) Appl. No.: 15/965,109

(22) Filed: Apr. 27, 2018

(65) Prior Publication Data

US 2018/0310957 A1 Nov. 1, 2018

Related U.S. Application Data

(60) Provisional application No. 62/491,770, filed on Apr. 28, 2017.

(51) Int. Cl.
*A61B 17/34* (2006.01)
*A61M 39/02* (2006.01)
(Continued)

(52) U.S. Cl.
CPC .......... *A61B 17/3423* (2013.01); *A61L 29/02* (2013.01); *A61M 25/001* (2013.01); *A61M 25/005* (2013.01); *A61M 25/0012* (2013.01); *A61M 25/0108* (2013.01); *A61M 39/0247* (2013.01); *B29D 23/00* (2013.01); *A61B 2017/00526* (2013.01); *A61B 2017/00853* (2013.01); *A61B 2017/00942* (2013.01); (Continued)

(58) Field of Classification Search
CPC .............. A61M 25/005; A61M 25/001; A61M 25/0012; A61B 17/3423; A61B 17/0218; A61B 17/0225
USPC .................................................. 600/201–225
See application file for complete search history.

(56) References Cited

U.S. PATENT DOCUMENTS 4,224,937 A 9/1980 Gordon
4,362,156 A 12/1982 Feller, Jr. et al.
(Continued)

FOREIGN PATENT DOCUMENTS

EP 0709108 A2 5/1996
WO 199839047 A1 9/1998
(Continued)

OTHER PUBLICATIONS

European Search Report dated Jul. 1, 2016 for EP12793304.2.
(Continued)

*Primary Examiner* — Eduardo C Robert
*Assistant Examiner* — Tara Rose E Carter
(74) *Attorney, Agent, or Firm* — Stoel Rives LLP

(57) ABSTRACT

The present disclosure illustrates an introducer sheath with a partially annealed metal frame. The introducer sheaths described herein include a hub coupled to a shaft. The shaft comprises a braided wire frame with (i) an annealed distal portion that prevents the braided wire frame from unraveling at a distal end, and (ii) a second portion that is unannealed; a jacket encompassing the braided wire frame; and a liner forming an inner wall.

21 Claims, 9 Drawing Sheets

(51) Int. Cl.
*A61M 25/00* (2006.01)
*A61M 25/01* (2006.01)
*A61L 29/02* (2006.01)
*B29D 23/00* (2006.01)
*B29K 77/00* (2006.01)
*A61B 17/02* (2006.01)
*A61M 39/06* (2006.01)
*A61B 17/00* (2006.01)

(52) U.S. Cl.
CPC ............... *A61B 2017/0225* (2013.01); *A61M 2039/0258* (2013.01); *A61M 2039/0273* (2013.01); *A61M 2039/0276* (2013.01); *A61M 2039/0279* (2013.01); *A61M 2039/062* (2013.01); *A61M 2039/0626* (2013.01); *A61M 2205/0238* (2013.01); *A61M 2207/00* (2013.01); *B29K 2077/00* (2013.01)

(56) References Cited

U.S. PATENT DOCUMENTS

| | | | |
|---|---|---|---|
| 4,705,511 A | 11/1987 | Kocak | |
| 4,862,891 A | 9/1989 | Smith | |
| 4,976,689 A | 12/1990 | Buchbinder et al. | |
| 4,997,421 A | 3/1991 | Palsrok et al. | |
| 5,069,674 A | 12/1991 | Fearnot et al. | |
| 5,180,376 A | 1/1993 | Fischell | |
| 5,324,262 A | 1/1994 | Fischell et al. | |
| 5,360,432 A | 11/1994 | Shturman | |
| 5,413,562 A | 5/1995 | Swauger | |
| 5,423,774 A | 6/1995 | Fischell et al. | |
| 5,454,795 A | 10/1995 | Samson | |
| 5,484,425 A | 1/1996 | Fischell et al. | |
| 5,496,344 A | 3/1996 | Kanesaka et al. | |
| 5,514,236 A | 5/1996 | Avellanet et al. | |
| 5,531,721 A | 7/1996 | Pepin et al. | |
| 5,630,806 A | 5/1997 | Inagaki et al. | |
| 5,658,264 A | 8/1997 | Samson | |
| 5,700,253 A * | 12/1997 | Parker ............... A61M 25/0012 604/524 |
| 5,702,373 A | 12/1997 | Samson | |
| 5,704,926 A | 1/1998 | Sutton | |
| 5,796,044 A | 8/1998 | Cobian et al. | |
| 5,827,230 A | 10/1998 | Bieman | |
| 5,827,239 A | 10/1998 | Dillon et al. | |
| 5,863,366 A | 1/1999 | Snow | |
| 5,879,499 A | 3/1999 | Corvi | |
| 5,891,114 A | 4/1999 | Chien et al. | |
| 5,927,345 A | 7/1999 | Samson | |
| 5,944,697 A | 8/1999 | Biche | |
| 5,947,940 A | 9/1999 | Beisel | |
| 5,951,929 A * | 9/1999 | Wilson ............... A61M 25/0009 264/138 |
| 5,957,974 A | 9/1999 | Thompson et al. | |
| 5,976,120 A | 11/1999 | Chow et al. | |
| 6,053,904 A * | 4/2000 | Scribner ............ A61M 25/0017 604/104 |
| 6,152,912 A | 11/2000 | Jansen et al. | |
| 6,165,163 A | 12/2000 | Chien et al. | |
| 6,264,684 B1 | 7/2001 | Banas et al. | |
| 6,338,725 B1* | 1/2002 | Hermann ......... A61B 17/12036 604/164.01 |
| 6,533,770 B1 | 3/2003 | Lepulu et al. | |
| 6,824,553 B1 | 11/2004 | Samson et al. | |
| 6,863,674 B2 | 3/2005 | Kasahara et al. | |
| 6,939,337 B2 | 9/2005 | Parker et al. | |
| 6,945,956 B2 | 9/2005 | Waldhauser et al. | |
| 7,083,588 B1 | 8/2006 | Shmuelwitz et al. | |
| 7,112,298 B2 | 9/2006 | Kampa et al. | |
| 7,320,697 B2 | 1/2008 | Demond | |
| 7,331,966 B2 | 2/2008 | Soma et al. | |
| 7,438,712 B2 | 10/2008 | Chouinard | |
| 7,618,430 B2 | 11/2009 | Scheib | |
| 7,655,021 B2 | 2/2010 | Brasington et al. | |
| 7,815,762 B2 | 10/2010 | Lentz et al. | |
| 7,905,877 B1* | 3/2011 | Jimenez ............ A61M 25/0012 604/525 |
| 8,034,045 B1 | 10/2011 | Lyons | |
| 8,262,625 B1 | 9/2012 | Fischell et al. | |
| 8,348,925 B2 | 1/2013 | Fischell et al. | |
| 2001/0010247 A1 | 8/2001 | Snow | |
| 2001/0044633 A1 | 11/2001 | Klint | |
| 2001/0049491 A1 | 12/2001 | Shimada | |
| 2002/0169377 A1 | 11/2002 | Khairkhahan et al. | |
| 2002/0198492 A1 | 12/2002 | Miller et al. | |
| 2003/0093060 A1 | 5/2003 | Kempf | |
| 2003/0225365 A1 | 12/2003 | Greff et al. | |
| 2003/0229313 A1 | 12/2003 | Bieman | |
| 2004/0010243 A1 | 1/2004 | Klint | |
| 2004/0068249 A1 | 4/2004 | Kampa et al. | |
| 2004/0116848 A1 | 6/2004 | Gardeski et al. | |
| 2004/0116960 A1 | 6/2004 | Demond et al. | |
| 2004/0143239 A1 | 7/2004 | Zhou et al. | |
| 2004/0153049 A1 | 8/2004 | Hewitt et al. | |
| 2004/0236346 A1 | 11/2004 | Parker | |
| 2005/0021022 A1 | 1/2005 | Sturm et al. | |
| 2005/0060017 A1 | 3/2005 | Fischell et al. | |
| 2005/0084672 A1 | 4/2005 | O'Brien | |
| 2005/0149060 A1 | 7/2005 | Thorstenson et al. | |
| 2005/0228479 A1 | 10/2005 | Pavcnik et al. | |
| 2005/0283136 A1 | 12/2005 | Skarda | |
| 2006/0064054 A1 | 3/2006 | Sakakine et al. | |
| 2006/0089618 A1 | 4/2006 | McFerran et al. | |
| 2006/0095050 A1 | 5/2006 | Hartley et al. | |
| 2006/0155302 A1 | 7/2006 | Sisken et al. | |
| 2007/0118207 A1 | 5/2007 | Amplatz et al. | |
| 2007/0185521 A1 | 8/2007 | Bui et al. | |
| 2007/0219500 A1 | 9/2007 | Wright et al. | |
| 2008/0051758 A1 | 2/2008 | Rioux et al. | |
| 2008/0097516 A1 | 4/2008 | Chang et al. | |
| 2008/0243081 A1 | 10/2008 | Nance et al. | |
| 2009/0018525 A1 | 1/2009 | Waite et al. | |
| 2009/0054845 A1 | 2/2009 | Puhasmagi et al. | |
| 2009/0157162 A1 | 6/2009 | Chow et al. | |
| 2009/0234295 A1 | 9/2009 | Lampropoulos et al. | |
| 2009/0240202 A1 | 9/2009 | Drasler et al. | |
| 2009/0287182 A1* | 11/2009 | Bishop ............... A61M 25/0662 604/509 |
| 2009/0306591 A1 | 12/2009 | Amisar et al. | |
| 2009/0306603 A1 | 12/2009 | Bierman et al. | |
| 2010/0016837 A1 | 1/2010 | Howat | |
| 2010/0049168 A1 | 2/2010 | Parker et al. | |
| 2011/0160702 A1 | 6/2011 | Jimenez et al. | |
| 2011/0245775 A1 | 10/2011 | Tekulve | |
| 2012/0215174 A1 | 8/2012 | Fischell et al. | |
| 2012/0265282 A1 | 10/2012 | Fischell et al. | |
| 2012/0310212 A1 | 12/2012 | Fischell et al. | |
| 2013/0079746 A1 | 3/2013 | Fischell et al. | |

FOREIGN PATENT DOCUMENTS

| | | |
|---|---|---|
| WO | 2004096335 | 11/2004 |
| WO | 2008051771 A1 | 5/2008 |
| WO | 2009045276 | 4/2009 |

OTHER PUBLICATIONS

Extended European Search Report dated Sep. 26, 2014 for EP12793304.2.
Extended European Search Report dated Sep. 28, 2015 for EP13769139.0.
International Search Report and Written Opinion dated Apr. 25, 2013 for PCT/US2013/020941.
International Search Report and Written Opinion dated Jul. 18, 2013 for PCT/US2013/033840.
International Search Report and Written Opinion dated Aug. 7, 2012 for PCT/US2012/035268.
International Search Report and Written Opinion dated Aug. 17, 2018 for PCT/US2018/029962.
International Search Report and Written Opinion dated Sep. 24, 2012 for PCT/US2012/043243.

(56) References Cited

OTHER PUBLICATIONS

International Search Report and Written Opinion dated Nov. 8, 2012 for PCT/US2012/40391.
Notice of Allowance dated Jul. 9, 2013 for U.S. Appl. No. 13/150,308.
Notice of Allowance dated Jul. 26, 2013 for U.S. Appl. No. 13/431,526.
Notice of Allowance dated Oct. 16, 2012 for U.S. Appl. No. 13/032,876.
Office Action dated Feb. 21, 2013 for U.S. Appl. No. 13/150,308.
Office Action dated Mar. 1, 2012 for U.S. Appl. No. 13/032,876.
Office Action dated Mar. 6, 2013 for U.S. Appl. No. 13/431,526.
Office Action dated Mar. 19, 2013 for U.S. Appl. No. 13/085,951.
Office Action dated May 25, 2012 for U.S. Appl. No. 13/032,876.
Office Action dated Jun. 3, 2013 for U.S. Appl. No. 13/349,060.
Office Action dated Sep. 21, 2012 for U.S. Appl. No. 13/150,308.
Office Action dated Dec. 8, 2011 for U.S. Appl. No. 13/032,876.
Ishmaku, et al.,Deformation Induced Nanostructure and Texture in MP35N Alloys, Journal of Materials Science 39 ,2004 ,5417-5420.
European Search Report dated Jan. 18, 2021 for EP18792048.3.

\* cited by examiner

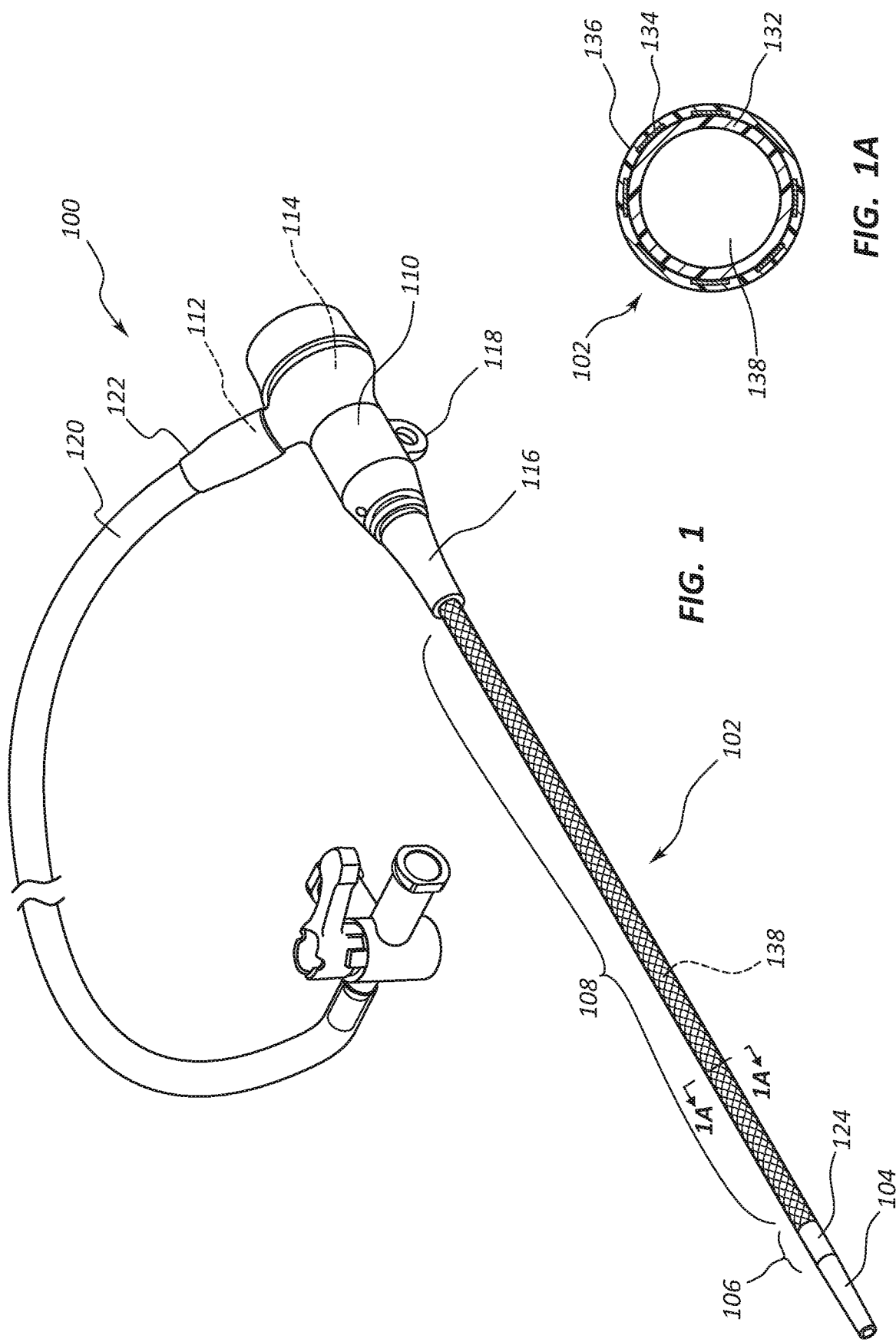

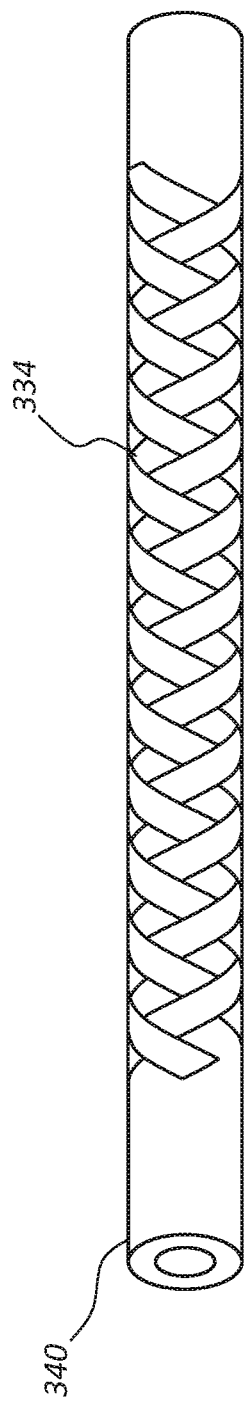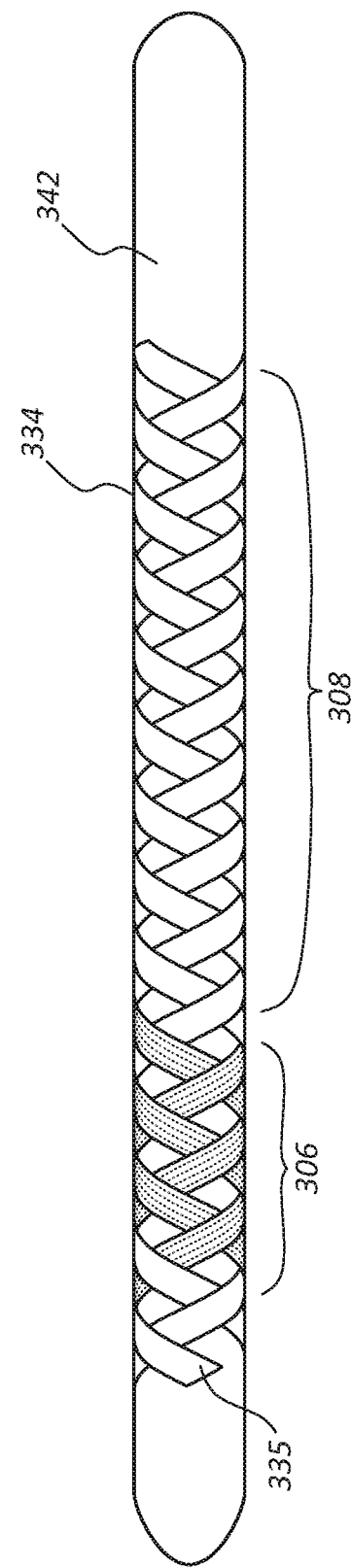
FIG. 3
FIG. 4

INTRODUCER WITH PARTIALLY ANNEALED REINFORCEMENT ELEMENT AND RELATED SYSTEMS AND METHODS

RELATED APPLICATIONS

This application claims priority to U.S. Provisional Application No. 62/491,770 titled "INTRODUCER WITH PARTIALLY ANNEALED REINFORCEMENT ELEMENT AND RELATED SYSTEMS AND METHODS," filed on Apr. 28, 2017, which is hereby incorporated by reference in its entirety.

TECHNICAL FIELD

The present disclosure relates generally to medical sheaths including introducer sheaths and methods to manufacture introducer sheaths. More particularly, some embodiments relate to introducer sheaths with a partially annealed reinforcement element.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 1 is a perspective view of an introducer sheath with a sheath shaft including a partially annealed reinforcement element, according to one embodiment.

FIG. 1A is a cross-sectional view, taken through line 1A-1A of a portion of the introducer sheath of FIG. 1.

FIG. 3 is a side view of a braided metal frame over a braiding core, according to one embodiment.

FIG. 4 is a side view of the braided metal frame of FIG. 3 disposed over an annealing mandrel.

DETAILED DESCRIPTION

Figure 2A:
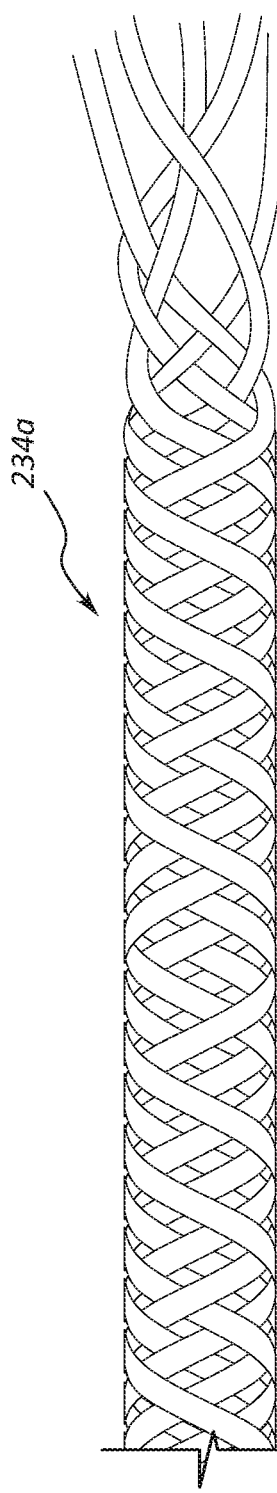
FIG. 2A is a side view of an unannealed braided metal frame.

This disclosure describes medical sheaths with a partially annealed reinforcement element, such as a partially annealed braided frame, and methods to manufacture such an introducer sheath. While embodiments herein refer to introducer sheaths, the same features may be included on other types of sheaths such as guiding sheaths.

Introducer sheaths are used in a variety of diagnostic and therapeutic procedures to provide access to a patient's vascular system. When an introducer sheath is placed in the vasculature, the introducer sheath may facilitate exchange of guidewires, catheters, contrast media, and various fluids while providing access to the vasculature and a hemostatic seal.

To facilitate the exchange of medical tools and fluids, the introducer sheath includes a hub configured to remain exterior to the patient's skin. The hub forms a chamber that may be accessed through various ports. For example, a hub may include a side port and an introducer bore. In some embodiments, the side port is fluidly coupled to a fluid channel that is controlled by a stop-cock. The fluid channel conveys fluids or medicaments to and from the hub. A practitioner may introduce guidewires, catheters, stents, balloons, and other articles and/or materials to be introduced into the patient through the introducer bore. A valve or a seal may maintain hemostasis of the introducer sheath while allowing a medical instrument to be introduced through the introducer bore into the chamber. The hub chamber is in fluid communication with a sheath shaft. The sheath shaft is inserted into the vasculature of the patient, and provides through the skin to the vasculature.

A problem with current sheaths is vascular access bleeding that sometimes occurs after the sheath shaft has been removed. In general, there is a relationship between the size of the outer diameter of the inserted sheath shaft and the risk of bleeding complications. Thus, sheaths shafts with thinner walls correlate to a decrease in the size of the outside diameter (and therefore a decrease in the size of the hole at the vascular entry site) without decreasing the size of the inside diameter of the sheath. Thus, thin walled sheaths may reduce bleeding complications when compared to thicker wall sheaths with the same inside diameter.

However, simply reducing the thickness of the walls of a sheath shaft introduces additional concerns. Specifically, with thinner walls, there may be a greater concern of kinking and deformation from a cylindrical shape. When a sheath shaft kinks, the passageway to the vascular system of a patient may be blocked. If a sheath shaft does not maintain its shape, medical instruments may not fit.

To maintain the shape of a thin walled sheath shaft, the wall of the shaft may be reinforced. A polymer shaft may be reinforced with a metal reinforcing element, such as a braided metal frame. The reinforcing element may thus increase the strength, stiffness, burst strength, creep resistance, and other properties of the shaft.

Braided metal frames may also have a desirable spring temper that both resists kinks and increases the capacity of the shaft to temporarily elastically deform, then spring back without creating a permanent kink. This, in turn, reduces instances where a kinked or deformed introducer shaft must be removed and replaced during a therapy.

While a braided metal frame may thus increase strength, stiffness, and kink recovery, spring temper metal in the braid may also tend to unravel or fray on the end of a cut piece of braid during assembly of the shaft. Though this tendency to unravel may be contained by use of a thicker polymer element around the braid, a thick polymer element also increases the wall thickness of the shaft. Annealing the braided metal frame, in the braided condition, may lessen the tendency of the metal to unraveling, allowing for use of a metal reinforcing braid with a thinner outer polymer element. In some applications, the entire braided metal frame is annealed. However, such an approach alters the spring temper of the entire braided metal frame and reduces the kink resistance and recovery characteristics of the braided metal frame. In other words, a spring temper reinforcing element imparts desirable properties to an introducer shaft, while an annealed reinforcing element may be easier to constrain within an outer polymer layer.

Certain embodiments of introducer sheaths described herein use a partially annealed braided metal frame to both reduce wall thickness and maintain a desirable wall stiffness, kink resistance, and kink recovery. Through only annealing a portion of the braided frame, the metal has a reduced tendency to unravel along the annealed portion and the braided frame maintains a desirable spring temper along the unannealed portions.

In some embodiments, an introducer shaft is coupled to a hub at a proximal end. The shaft forms a lumen that is in fluid communication with the chamber of the hub. The shaft may include a braided metal frame with an annealed distal portion and a second portion of the braided metal frame that is unannealed. The annealed distal portion reduced the tendency of the braided metal frame to unravel at a distal end. In some embodiments, the hub may prevent the braided metal frame from unraveling at the proximal end. In some embodiments, the braided metal frame may include an annealed proximal portion. An outer polymer member such as a jacket may encompass the braided wire reinforcing element, and an inner polymer member such as a liner may form an inside surface of the wall of the shaft.

Partially annealed introducer sheaths may be manufactured using the methods described in more detail below. In some embodiments, metal wires are braided to form a frame of a sheath shaft. A distal portion of the frame is annealed to prevent the frame from unraveling at a distal end. A liner and a jacket are reflowing or melt-bonded onto the frame, and a hub is overmolded around a proximal portion of the reflowed shaft. These methods may be done along a length sufficient to produce a plurality of introducer sheaths. For example, in some embodiments, a larger amount of wire may be braided along a nylon core to form a frame. The nylon core may be heated and stretched to reduce the diameter of the nylon core for removal of the frame. A plurality of portions along the frame may be annealed. The portions that are annealed may correspond to ends of each of a plurality of introducer sheaths to be formed from the initial braid. A liner and a jacket may be reflowed to the inner and outer surfaces of the frame. The frame may be cut at the annealed portions to form a plurality of sheath shafts such that the annealed portions are located at a distal end of each of the plurality of sheath shafts. A hub may be overmolded around a proximal portion of the sheath shafts.

The phrase "coupled to" is broad enough to refer to any suitable coupling or other form of interaction between two or more entities, including mechanical, fluidic and thermal interaction. Thus, two components may be coupled to each other even though they are not in direct contact with each other. The phrase "fluid communication" is used in its ordinary sense, and is broad enough to refer to arrangements in which a fluid (e.g., a gas or a liquid) can flow from one element to another element when the elements are in fluid communication with each other.

The terms "proximal" and "distal" are opposite directional terms. As used herein, the distal end of a device or component is the end of the component that is furthest from the physician during ordinary use. The proximal end refers to the opposite end, or the end nearest the physician during ordinary use. For example, the proximal end of an introducer sheath used in minimally invasive vascular treatment is the end accessible to a practitioner during use, while the distal end is disposed within a patient's vascular system when the sheath is placed into such a patient.

An assembler may be any person, system, or machine used in the manufacture of the introducer sheaths.

Embodiments may be understood by reference to the drawings, wherein like parts are designated by like numerals throughout. The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

FIG. 1 is a perspective view of an introducer sheath 100 comprising a sheath shaft 102 with a partially annealed reinforcement member, according to one embodiment. As shown, the introducer sheath 100 can include the sheath shaft 102 and a hub 110. The sheath shaft 102 is coupled to and in fluid communication with the hub 110. During some procedures, the hub 110 is intended to remain exterior of a patient, and the sheath shaft 102 is intended to at least partially be placed within the vascular system of the patient.

The hub 110 forms a chamber that may be accessed via a side port 112 or an introducer bore 114. A suture ring 118 is coupled to the hub 110 and provides a mechanism allowing a practitioner to grasp the introducer sheath 100 while allowing the introducer sheath 100 to be sutured or fastened to the patient once the introducer sheath 100 has been properly placed. The side port 112 and the introducer bore 114 provide entry for medical devices and fluids. For example, a physician may insert a dilator into the introducer bore 114 to assist with placing the introducer sheath 100. The dilator enters the introducer bore 114 through a seal or a valve that maintains hemostasis when the introducer sheath 100 in in communication with the vasculature. Similarly, a fluid channel 120 may couple to the side port 112, establishing a fluid passageway with the chamber of the hub 110. In some embodiments, a sleeve may be used to swage the fluid channel 120 onto the side port 112. A sleeve 122 may be placed over the fluid channel 120 onto the side port 112. Any medical instrument or fluids that enter the chamber of the hub 110 may continue through an opening at the hub distal end 116 into a sheath shaft lumen 138. Thus, the side introducer bore 114 and a lumen of the fluid channel 120 may both be in fluid communication with the sheath shaft lumen 138.

FIG. 1A is a cross-sectional view, taken through line 1A-1A of a portion of the introducer sheath 100, showing elements of the sheath shaft 102. With reference to FIGS. 1 and 1A, the sheath shaft 102 includes an annealed portion 106 and an unannealed portion 108. A tip 104 is coupled to the sheath shaft 102. A cuff 124 may overlap the tip-shaft joint to strengthen the joint. The sheath shaft 102 may be formed from a braided metal frame 134 with an exterior and interior surface coated with a polymer material. In the illustrated embodiment, a liner 132 is coupled to the interior surface of the braided metal frame 134 and defines the inside surface of the sheath shaft 102 and a jacket 136 is coupled to the exterior surface of the braided metal frame 134 and defines the outside surface of the sheath shaft 102. FIG. 1A may be understood as schematic in nature, though the liner 132, braided metal frame 134, and jacket 136 are shown as distinct layers, as further detailed below, the polymer materials of the liner 132 and jacket 136 may be melted and reflowed together, bonding to the braided metal frame 134 and each other and filling any openings in the braided metal frame 134.

The introducer sheath 100 may have a thinner wall when compared with traditional introducer sheaths. In some embodiments, the introducer sheath 100 may have an $$\frac{\text{inner diameter lower limit}}{\text{outer diameter upper limit}}$$

ratio of greater than 0.85. For example, an introducer sheath for a 4 French (4 F) needle or catheter may have an $$\frac{\text{inner diameter lower limit}}{\text{outer diameter upper limit}}$$

ratio of greater than 0.85, an introducer sheath for a 5 F needle or catheter may have an $$\frac{\text{inner diameter lower limit}}{\text{outer diameter upper limit}}$$

ratio of greater than 0.87, an introducer sheath for a 6 F needle or catheter may have an $$\frac{\text{inner diameter lower limit}}{\text{outer diameter upper limit}}$$

ratio of greater than 0.89, an introducer sheath for a 7 F needle or catheter may have an $$\frac{\text{inner diameter lower limit}}{\text{outer diameter upper limit}}$$

ratio of greater than 0.90. In some embodiments, the introducer sheath 100 may have an $$\frac{\text{inner diameter}}{\text{outer diameter}}$$

ratio ranging between 0.87 and 0.93. For example, an introducer sheath for a 4 F needle or catheter may have an average $$\frac{\text{inner diameter}}{\text{outer diameter}}$$

ratio ranging between 0.87 and 0.89, an introducer sheath for a 5 F needle or catheter may have an average $$\frac{\text{inner diameter}}{\text{outer diameter}}$$

ratio ranging between 0.89 and 0.90, an introducer sheath for a 6 F needle or catheter may have an average $$\frac{\text{inner diameter}}{\text{outer diameter}}$$

ratio ranging between 0.90 and 0.91, and an introducer sheath for a 7 F needle or catheter may have an average $$\frac{\text{inner diameter}}{\text{outer diameter}}$$

ratio ranging between 0.92 and 0.93.

The annealed portion 106 and the unannealed portion 108 of the sheath shaft 102 may correspond to portions along the length of the sheath shaft 102 where the braided metal frame 134 is annealed or unannealed, respectively. The term unannealed refers to portions of the braided metal frame 134 that retain or otherwise are configured with more spring temper than the annealed portion 106. The tip 104 may be coupled to the sheath shaft 302 adjacent the annealed portion 106. In some embodiments, the tip 104 lacks a metal frame, making the tip 104 more malleable to reduce trauma and increase trackability over a guidewire when the introducer sheath 100 enters the vascular system. In some embodiments, a cuff may be positioned across the joint between the tip 104 and the annealed portion 106. The cuff may smooth the transition between the tip 104 and the annealed portion 106 and increase the strength of the joint.

Figure 2B:
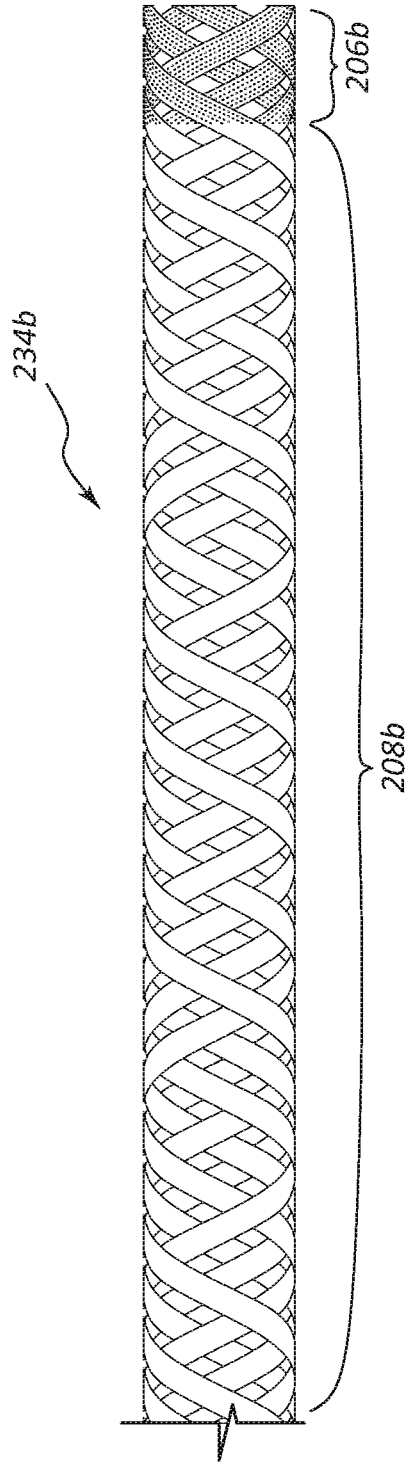
FIG. 2B is a side view of a partially annealed braided metal frame with an annealed distal portion.

FIG. 2A is a side view of an unannealed braided metal frame 234a and FIG. 2B is a side view of a partially annealed braided metal frame 234b with an annealed distal portion 206b. (In FIGS. 2A and 2B, analogous portions are designated with analogous reference numerals followed by an "a" or "b" corresponding to each figure.) The braided metal frames 234a and 234b of FIGS. 2A and 2B resembles the braided metal frame 134 of FIG. 1, described above, in certain respects. Accordingly, like features are designated with like reference numerals, with the leading digits incremented to "2." For example, the embodiment depicted in FIGS. 1 and 1A includes an unannealed portion 108 that may, in some respects, resemble the unannealed portions 208a and 208b of FIGS. 2A and 2B. Relevant disclosure set forth above regarding similarly identified features thus may not be repeated hereafter. Moreover, specific features of the braided metal frames 234a and 234b and related components shown in FIGS. 2A and 2B may not be shown or identified by a reference numerals in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the embodiments of FIGS. 2A and 2B. Any suitable combination of the features, and variations of the same, described with respect to the introducer sheath 100 and related components illustrated in FIGS. 1 and 1A can be employed with the embodiments and related components of FIGS. 2A and 2B, and vice versa. This pattern of disclosure applies equally to further embodiments depicted in subsequent figures and described hereafter, wherein the leading digits may be further incremented.

FIG. 2A illustrates how an unannealed metal frame 234a, having a spring temper, tends to unravel. The spring temper of the fibers of the unannealed metal frame 234a have a tendency to straighten themselves from the braided configuration due to the spring temper, and thus unravel if unconstrained.

FIG. 2B is a side view of a partially annealed braided metal frame 234b with an annealed portion 206b. The annealed portion 206b is located at the distal end of the braided metal frame 234b. Annealing the annealed portion 206b removes residual stresses and the spring temper of the braided metal frame 234b along the annealed portion 206b. When annealed, the fibers of the annealed portion 206b do not tend to self-straighten and unravel in the same manner as the unannealed fibers of the braided metal frame 234a of FIG. 2A.

The presence of the annealed portion 206b at the distal end of the braided metal frame 234b also helps maintain the braid along the unannealed portion 208b of the braided metal frame 234b. Though the fibers along the unannealed portion 208b retain their spring temper, interaction with adjacent fibers and with the annealed portion 206b mitigates the ability of these fibers to self-straighten such that they unravel. Thus, the annealed portion 206b may prevent the remaining unannealed portion 208b from unraveling like the unannealed braided metal frame 234a in FIG. 2A. Thus, the partially annealed braided metal frame 234b may maintain the spring temper of an unannealed braided metal frame along the majority of its length and while still tending to remain in its tubular braided shape without outside constraints that would be required to retain the shape of a wholly unannealed braided metal frame.

In some embodiments the annealed portion 206b may be from approximately 1/32 inches long to approximately 1/4 inches long, including from about 1/16 inches long to about 3/16 inches long and about 1/8 inches long.

FIGS. 3-9 illustrate various stages of manufacture of an introducer sheath with a partially annealed shaft, such as introducer 100 illustrated in FIG. 1. As noted in the explanation of the relationship of FIGS. 1 and 1A to FIGS. 2A and 2B, above, the elements and embodiments of FIGS. 3-9 may analogously relate to elements and embodiments of other figures. Again, like elements are referenced with like reference numerals with the leading digits incremented. Disclosure related in connection with one embodiment may analogously be applied to the other embodiments, and vice versa.

Further, FIGS. 3-9 depict certain exemplary manufacturing instruments that may be used to create an introducer sheath, such as introducer sheath 100. Additionally, the manufacturing instruments may be used in various method steps, including those steps depicted in FIG. 10.

FIG. 3 is a side view of a braided metal frame 334 over a braiding core 340, according to one embodiment. The braiding core 340 provides a surface for the wires to be braided around to form the braided metal frame 334.

The braided metal frame 334 may be made from wires with a desired spring temper. For example, tempered steel or brass wires may have a desired spring temper induced to increase their upper limit of elasticity. Steels used in the braided metal frame 334 may include stainless steel, low-alloy, medium-carbon steel, nitinol, and high-carbon steel including those with high yield strength. In some embodiments, one or more radiopaque strands of material may be used in the braided metal frame 334. For example one or more wires of palladium, platinum, depleted uranium, or high radiopaque wire may be weaved into the braided metal frame 334 for fluoroscopy identification. In some embodiments, marker bands may be integrated into the braided metal frame 334 for fluoroscopy identification. The spring temper of the wires may allow the braided metal frame 334 to return to its original shape despite deflection, deformation, and/or twisting. In some embodiments, the braided metal frame 334 may include flat wires. In other embodiments, the braided metal frame 334 may include round wires. In yet other embodiments, the braided metal frame 334 may include a combination of flat and round wires. Each strand of the braided metal frame 334 may include one or more wires. For example, a five-strand bobbin may be used to braid a frame with five wires in every braid. The tightness of the weave of the braided metal frame 334 may be altered to adjust the stiffness and flexibility of the introducer sheath.

The braiding core 340 may comprise a thermoplastic that becomes pliable or moldable above a specific temperature and solidifies upon cooling. For example, in some embodiments, nylon may be extruded to form the braiding core 340. The diameter of the braiding core 340 corresponds to the inside diameter of the braided metal frame 334, which thus relates (when adjusted for polymer lines and jackets) to the finished outside and inside diameters of a finished sheath shaft (such as sheath shaft 102 of FIG. 1) of an introducer sheath. When the braided metal frame 234 has been created, an assembler may heat the braiding core 340 to a point that the thermoplastic becomes pliable, and stretch the braiding core 340. Stretching the braiding core 340 causes the braiding core 340 to neck down, resulting in a longer core with a smaller diameter. The smaller diameter allows an assembler to easily remove the braiding core 340 from the braided metal frame 334.

FIG. 4 is a side view of the braided metal frame 334 disposed over an annealing mandrel 342. After the braiding core 340 of FIG. 3 is removed, an assembler may load the braided metal frame 334 on the annealing mandrel 342 to anneal at least a portion of the braided metal frame 334.

In some embodiments, an assembler uses electromagnetic waves such as radio frequency (RF) or microwaves to selectively anneal portions of the braided metal frame 334. For example, RF radiation may be applied to a portion of the braided metal frame 334 to anneal the material along that portion to form an annealed portion 306. The braided metal frame 223 may be selectively annealed by transferring heat to the braided metal frame 223 using a heated element or a flame. The annealed portion 306 may be disposed near the distal tip 335 of the braided metal frame 334. The annealing process allows for crystalline restructuring between adjacent braids of the annealed portion 306. The crystalline restructuring of the annealed portion 306, such as at the intersection between adjacent braids, may tend to prevent the unannealed portion 108 from unraveling. Additionally, annealing may reduce the tendency of the braids to straighten out, also tending to prevent unraveling.

The length of the annealed portion 306 may vary based on application. In some embodiments, the annealed portion 306 may be from approximately 1/32 inches long to approximately 1/4 inches long, including from about 1/16 inches long to about 3/16 inches long and about 1/8 inches long. In some embodiments, a plurality of portions on the length of a long braided metal frame may be annealed. The long braided metal frame may subsequently be cut to form multiple braided metal frames for inclusion in introducer sheath shafts. The positions of the plurality of annealed portions along the long braided metal frame may thus ultimately correspond to portions that will be disposed as distal ends of a plurality of introducer sheath shafts.

Figure 5A:
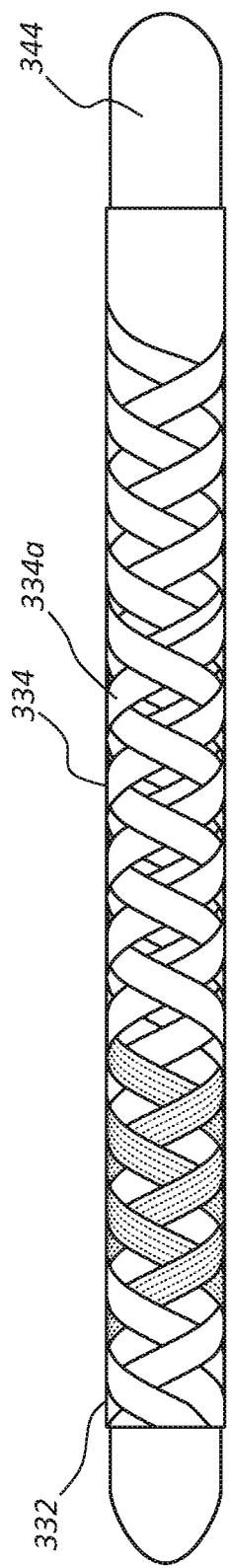
FIG. 5A is a side view of the braided metal frame of FIGS. 3 and 4 disposed over a liner loaded on a low surface friction mandrel.

FIG. 5A is a side view of the braided metal frame 334 over a liner 332 loaded on a low surface friction mandrel 344. Low surface friction mandrel 344 may be formed from or coated with low friction materials to ease loading and removal of the liner 332 and braided metal frame 334. For example, in some embodiments, the low surface friction mandrel 344 may be a polytetrafluoroethylene (PTFE) to slide a stainless steel metal frame onto. In some embodiments, lubricants may be used to reduce the friction on the surface of the low surface friction mandrel 344.

The liner material may comprise polyamide resins configured to seal the interior surface of the braided metal frame 334. The liner 332 can include a surface comprising a lubricious polymeric material. For example, the material can comprise any bio-compatible material having low frictional properties (e.g., TEFLON®, PTFE, fluorinated ethylene propylene (FEP), polyethylene, polyamide, ethylene chlorotrifluoro-ethylene, ethylene tetrafluoroethylene, PVDF).

Figure 5B:
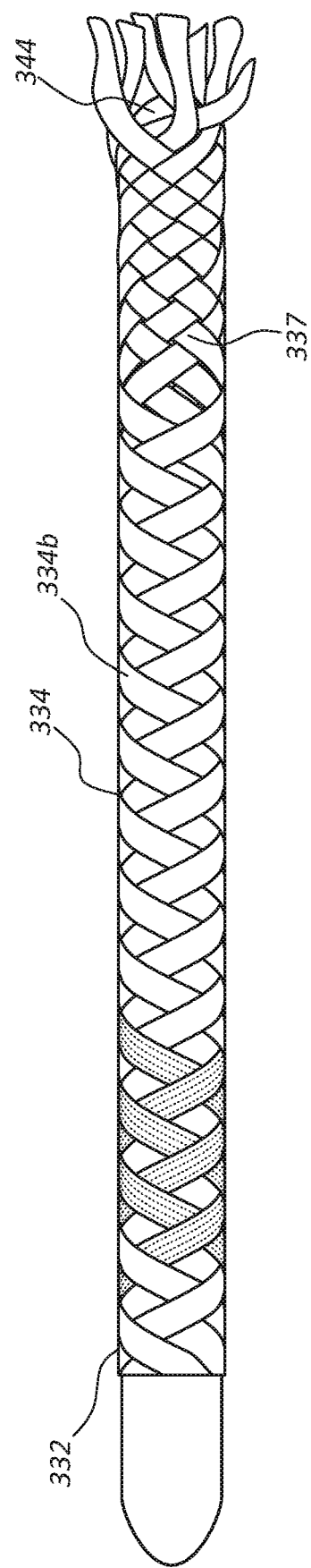
FIG. 5B is a side view of the braided metal frame and liner of FIG. 5A loaded on a low surface friction mandrel.

As shown, when the braided metal frame 334 is slid over the liner 332, the fibers of the braided metal frame 334 may tend to bunch forming a bunched section 334a. Such bunching may result in the braided metal frame 334 becoming non-uniform. Non-uniformity, in turn, may cause inconsistencies along the surface of the introducer sheath shaft, and alter the flexibility along the introducer sheath shaft. Therefore, in some embodiments, the braided metal frame 334 may be stretched after being placed on the liner 332 to restore uniformity as shown in FIG. 5B. In some embodiments, the braided metal frame 334 may be braided directly onto the mandrel and annealing may occur while braiding. This may prevent bunching of the braided metal frame 334.

FIG. 5B is a side view of the braided metal frame 334 with a straightened section 334b (e.g., the bunched section of FIG. 5A stretched to restore uniformity) disposed over the liner 332 and loaded on the low surface friction mandrel 344. As shown, an assembler may stretch the braided metal frame 334 until it is approximately uniform. A proximal portion 337 may be twisted down against the liner 332 and low surface friction mandrel 344 after stretching. The twisting may secure the proximal portion 337 in place and cause the remainder of the braided metal frame 334 to maintain its shape and position. The uniformity of the braided metal frame 334 results in a similar flexibility, kink resistance, and diameter along the entire length of the introducer sheath shaft. The step of stretching the braided metal frame 334 to restore uniformity may not be needed in instances wherein the braided metal frame 334 is slid over the liner 332 in such a manner as to retain its uniform consistency.

Figure 6A:
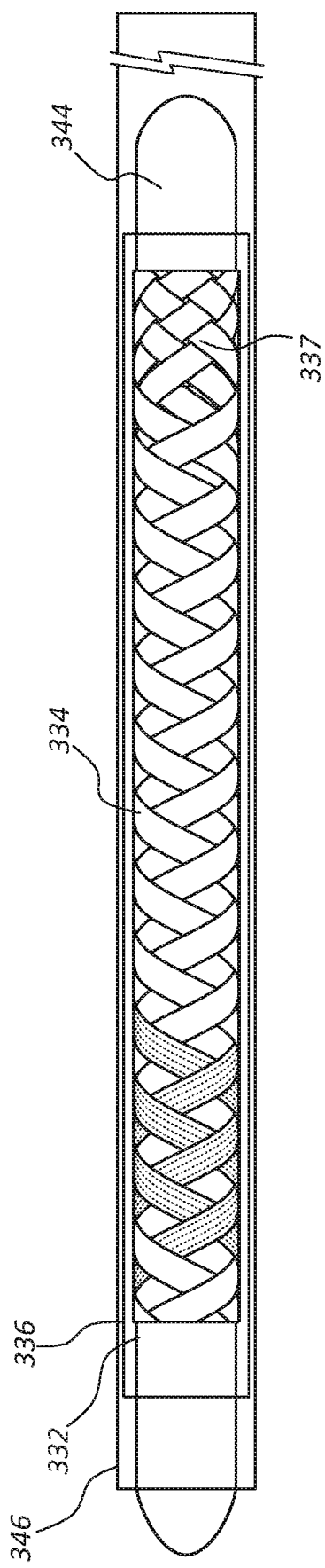
FIG. 6A is a side view of the braided metal frame, liner, and low surface friction mandrel of FIG. 5B with a jacket and fluorinated ethylene propylene (FEP) shell.

FIG. 6A is a side view of the braided metal frame 334 and the liner 332 loaded on the low surface friction mandrel 344, with a jacket 336 disposed over the braided metal frame 334 and an FEP shell 346 disposed over the jacket 336. The jacket 336 may have a hydrophilic coating and a larger diameter than the braided metal frame 334. The FEP shell 346 may have a larger diameter than the jacket 336 and encompass the jacket 336, braided metal frame 334, and liner 332.

Figure 6B:
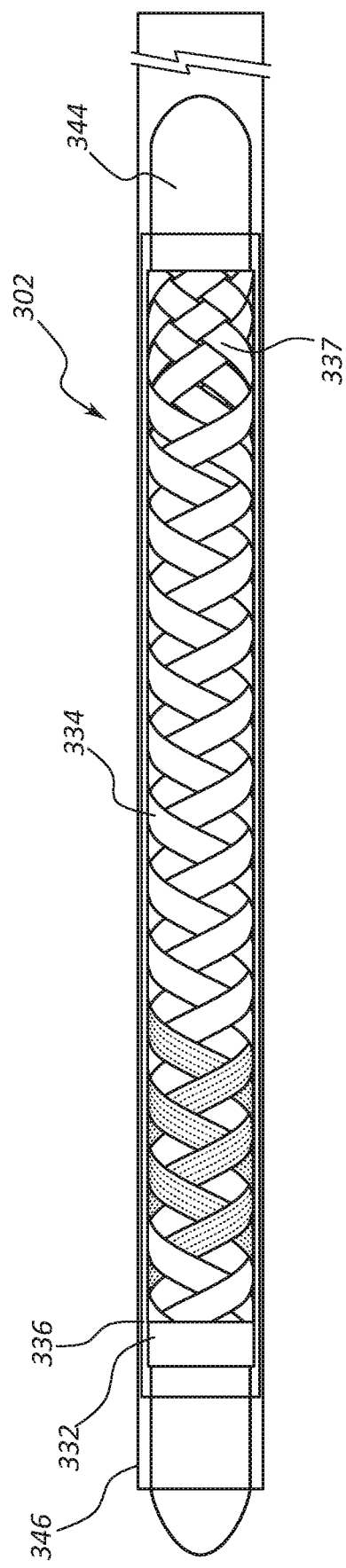
FIG. 6B is a side view the braided metal frame, liner, jacket, and FEP shell of FIG. 6A in a reflowed state to create a sheath assembly.

All of the components may be heated to melt or reflow the liner 332 and the jacket 336 as shown in FIG. 6B. Heating the FEP shell 346 causes it to shrink, reducing its diameter. The reduced diameter of the FEP shell 346 causes the sidewalls of the FEP shell 346 to apply pressure to the encompassed elements (i.e., the jacket 336, braided metal frame 334, and liner 332). The reflow temperature is within a range that causes the jacket 336 and liner 332 to melt, but not the FEP shell 346. Thus, the jacket 336 and liner 332 are reflowed to the metal frame 334 to create a composite conduit forming a sheath shaft 302.

Figure 7:
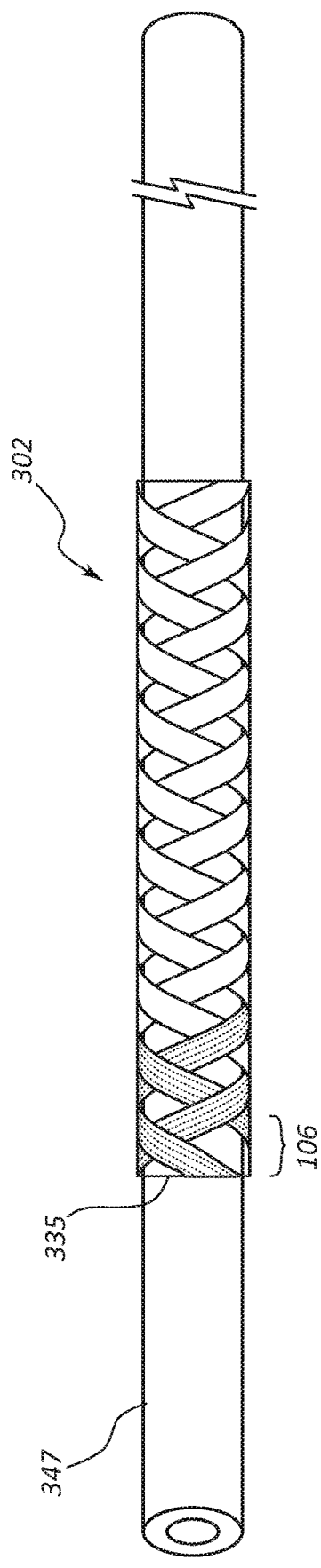
FIG. 7 is a side view of the assembly of FIG. 6B loaded on a cutting mandrel.

FIG. 7 is a side view of the sheath shaft 302 loaded on a cutting mandrel 347. As shown, the distal and proximal ends of the sheath shaft 302 have been cut and removed. In some embodiments, part of the annealed portion 306 is removed, ensuring that the distal tip 335 of the braided metal frame 334 comprises an edge of the annealed portion 306.

Figure 8:
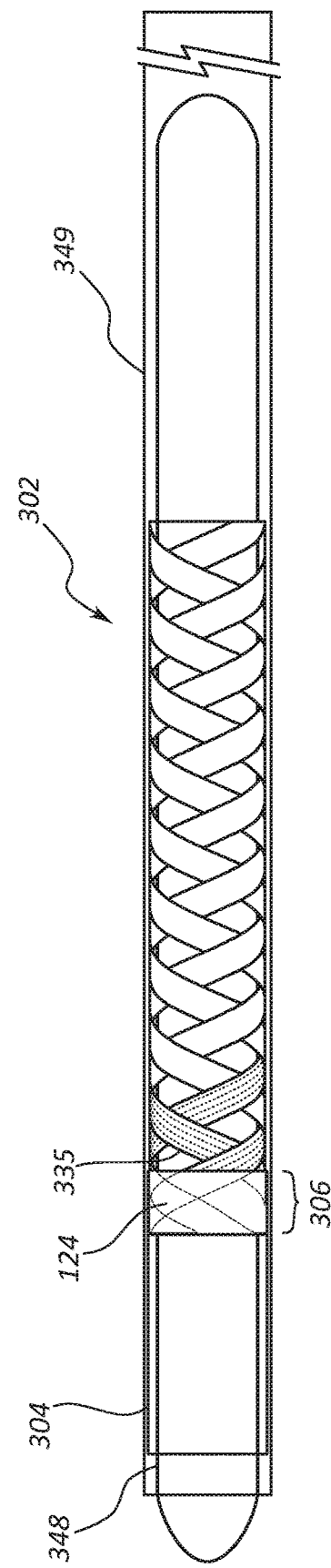
FIG. 8 is a side view of the assembly of FIGS. 6B and 7 with a tip coupled to the distal tip, according to one embodiment.

FIG. 8 is a side view of the sheath shaft 302 with a tip 304 coupled to the composite conduit sheath shaft 302 adjacent the distal tip 335 of the braided metal frame 334. The tip 304 may comprise a polymeric material configured to be malleable to reduce trauma when the introducer sheath enters the vascular system and increase trackability of the introducer over a guidewire. A butt joint may couple the tip 304 to the sheath shaft 302. A butt joint ensures smoothness through the transition from the tip 304 to the sheath shaft 302. In some embodiments, the tip 304 may overlap the sheath shaft 302. In some embodiments, a cuff 124 may overlap the tip 304 and the annealed section of the sheath shaft 302 to strengthen the butt joint. Coupling the tip 304 to the sheath shaft 302 may be accomplished via a similar method as was described with reference to FIGS. 6A-6B. Specifically, the components may be loaded on a low surface friction mandrel 348 (not necessarily the same low surface friction mandrel 344 discussed above, though it may be). An FEP shell 349 (not necessarily the same FEP shell 346 discussed above) may encompass the tip 304 and the sheath shaft 302. Heat may cause the FEP shell 349 to shrink and apply pressure while the tip 304 melts to the sheath shaft 302.

Figure 9:
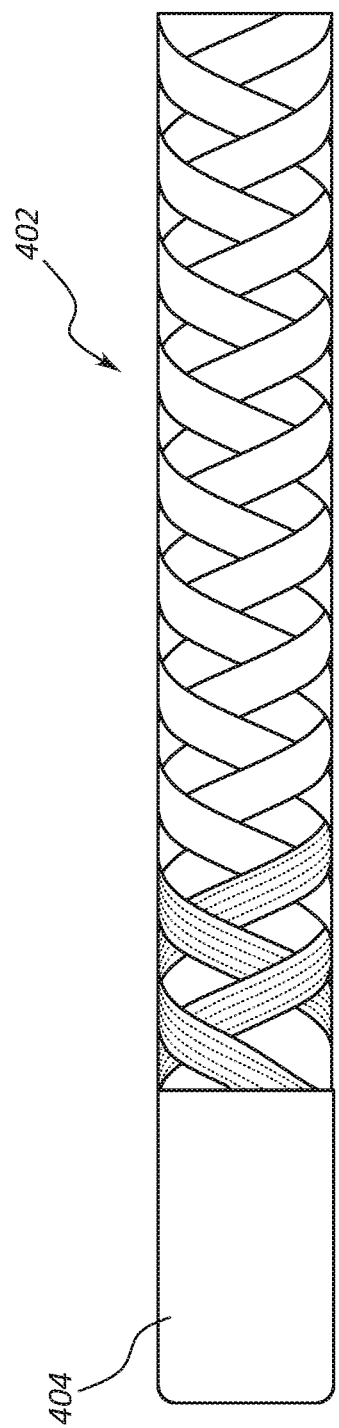
FIG. 9 is a side view of the sheath shaft with an overmolded tip.

FIG. 9 is a side view of the sheath shaft 402 with an overmolded tip 404. As shown, the tip 404 may couple to the sheath shaft 402 at a distal end and may be coupled via an overmolding process. Similarly, the hub (not shown) may be overmolded at a proximal end of the sheath shaft 402. In some embodiments the tip 404 may be more radiopaque than other components to facilitate imaging.

Figure 10:
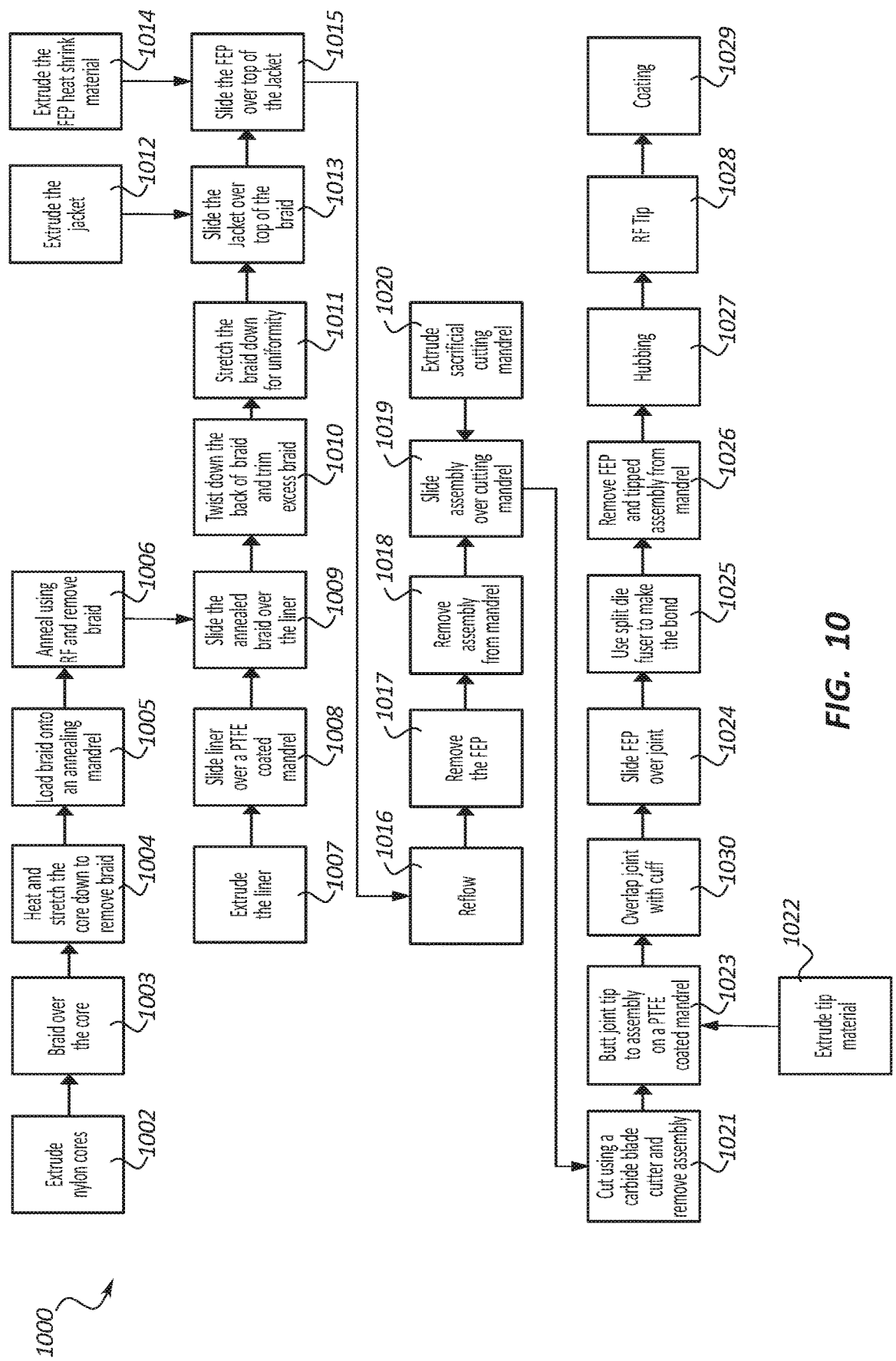
FIG. 10 is a flow diagram of a method of manufacturing an introducer sheath, according to one embodiment.

FIG. 10 is a flow diagram of an example of a method 1000 of manufacturing an introducer sheath, according to one embodiment. The steps shown in FIG. 10 may be optional and not necessarily including in each process. Further, various steps may be completed in different sequences from those shown in FIG. 10.

In the illustrated process of FIG. 10, an assembler extrudes 1002 a nylon core and braids 1003 a metal fame over the core. The assembler then heats and stretches 1004 the core and removes the braid. The assembler loads 1005 the braid onto an annealing mandrel. RF anneals 1006 a portion of the braid.

A liner is extruded 1007 and slides 1008 over a PTFE-coated mandrel. The assembler slides 1009 the annealed braid over the liner. The back of the braid is twisted 1010 down, and any excess braid is trimmed. The assembler stretches 1011 the braid for uniformity. The assembler extrudes 1012 a jacket, and extrudes 1014 an FEP heat shrink shell. The assembler slides 1013 the extruded jacket over top of the braid, and slides 1015 the FEP shell over the jacket. The assembly is exposed to heat, causing the liner and the jacket to reflow 1016.

The FEP shell is removed 1017, and the assembly is removed 1018 from the mandrel. The assembler extrudes 1020 a sacrificial cutting mandrel and slides 1019 the assembly over the cutting mandrel. The assembler uses a carbide blade to cut 1021 the ends of the assembly. The assembler extrudes 1022 a tip and joins 1023 the assembly to the tip using a butt joint. The assembler may place a cuff overlapping 1030 the butt joint for additional strength. The assembler slides 1024 an FEP shell over the joint and uses a split die fuser to bond 1025 the tip to the assembly. The assembler removes 1026 the assembly from the FEP shell and the mandrel and overmolds a hub 1027 and a radiopaque tip 1028. The assembler coats 1029 the assembly with a hydrophilic coating.

Figure 11:
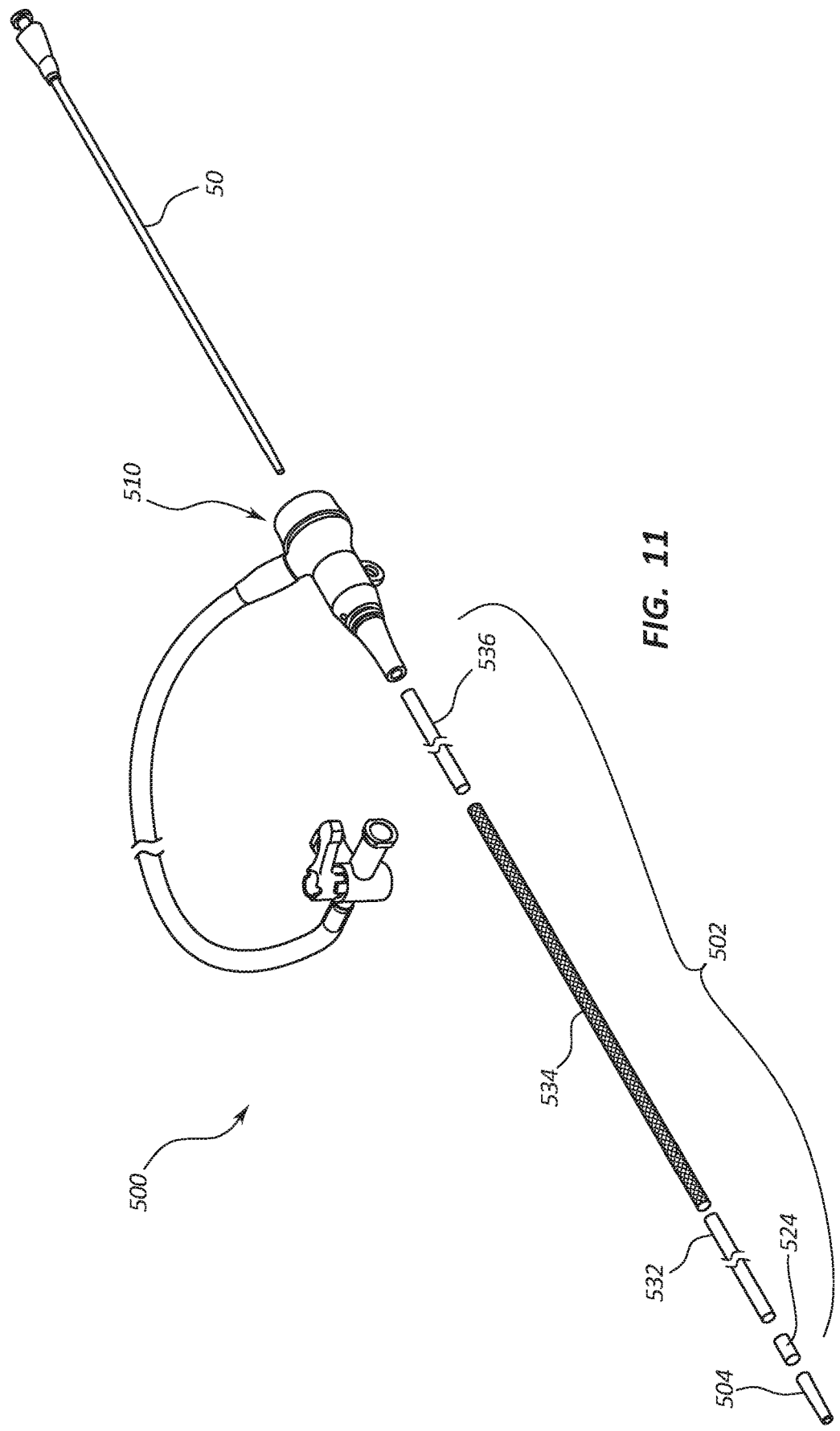
FIG. 11 is an exploded view of an introducer sheath with a shaft including a partially annealed reinforcement element, according to one embodiment.

FIG. 11 is an exploded view of an introducer sheath 500 with a partially annealed sheath shaft 502, according to one embodiment. A hub 510 may provide access to the sheath shaft 502 for medical instruments such as a dilator 50. Further, the sheath shaft 502 may comprise a liner 532, braided metal frame 534, jacket 536, and cuff 524. The sheath shaft 502 elements may be coupled via a reflow process that melt-bonds the elements together. A tip 504 is coupled to the sheath shaft 502.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "near." For each such reference, it is to be understood that, in some embodiments, the value, feature, or characteristic may be specified without approximation. For example, where qualifiers such as "near" and "approximately" are used, these terms include within their scope the qualified words in the absence of their qualifiers. For example, where the term "approximately aligned" is recited with respect to a feature, it is understood that in further embodiments, the feature can have a precisely aligned configuration.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A sheath comprising:
　a hub forming a chamber and comprising:
　　a side port in fluid communication with the chamber, and
　　an introducer bore with a seal to maintain hemostasis of the introducer sheath while allowing a medical instrument to be introduced through the introducer bore into the chamber; and
　a shaft coupled to the hub at a proximal end, the shaft forming a lumen that is in fluid communication with the chamber of the hub, the shaft comprising:
　　a braided wire frame with an annealed distal portion preventing the braided wire frame from unraveling at a distal end during assembly, a second portion of the braided wire frame being unannealed, the second portion maintaining physical properties of spring temper wire;
　　a jacket encompassing the braided wire frame, and
　　a liner forming an inner wall, the liner encompassed by the braided wire frame,
　wherein the shaft is 7 French and comprises an inner diameter to outer diameter ratio between 0.92 and 0.93.

2. The sheath of claim 1, wherein the hub is overmolded around a proximal portion of the shaft.

3. The sheath of claim 1, wherein the hub prevents a proximal end of the braided wire frame from unraveling.

4. The sheath of claim 1, wherein a proximal portion of the braided wire is annealed.

5. The sheath of claim 1, wherein the jacket and the liner are reflowed to the braided wire frame.

6. The sheath of claim 1, wherein the jacket comprises a hydrophilic coating.

7. The sheath of claim 1, wherein the braided wire frame comprises stainless steel.

8. The sheath of claim 1, wherein the braided wire frame comprises flat wires and round wires.

9. The sheath of claim 1, further comprising a radiopaque tip coupled to a distal end of the shaft.

10. A method of manufacturing an introducer sheath, comprising:
　braiding metal wires to form a non-expandable frame of a sheath shaft;
　annealing a distal portion of the frame to prevent the frame from unraveling at a distal end during assembly;
　reflowing a liner to an interior surface of the frame;
　reflowing a jacket to an exterior surface of the frame; and
　overmolding a hub around a proximal portion of the frame to prevent the frame from unraveling at a proximal end, the hub having a chamber in fluid communication with a hollow conduit formed from reflowing the liner and jacket to the frame, a side port in fluid communication with the chamber, and an introducer bore with a seal to maintain hemostasis of the introducer sheath while allowing a medical instrument to be introduced through the introducer bore into the chamber, wherein the sheath shaft is 7 French and comprises an inner diameter to outer diameter ratio between 0.92 and 0.93.

11. The method of claim 10, further comprising:

extruding a nylon core, wherein braiding the metal wires is performed over the nylon core causing the frame to have an interior diameter equivalent to a diameter of the nylon core;

heating and stretching the nylon core to reduce the diameter of the nylon core; and sliding the frame off of the nylon core.

12. The method of claim 10, wherein annealing the distal portion of the frame comprises:

loading the frame onto an annealing mandrel; and applying radio frequency energy to the distal portion of the frame.

13. The method of claim 10, wherein reflowing the liner and the jacket comprises:

loading the liner onto a mandrel;

sliding the frame over the liner;

sliding the jacket over a top of the frame; and applying heat and pressure to the jacket.

14. The method of claim 13, wherein the mandrel is coated with polytetrafluoroethylene.

15. The method of claim 13, further comprising twisting the proximal end of the frame and trimming excess metal wires.

16. The method of claim 13, further comprising stretching the frame for uniformity.

17. The method of claim 13, wherein applying heat and pressure to the jacket is done using fluorinated ethylene propylene tubing.

18. The method of claim 10, further comprising adjoining a tip to the distal end of the sheath shaft.

19. The method of claim 10, further comprising overmolding a radiopaque tip on the distal end of the sheath shaft.

20. The method of claim 10, wherein only a distal portion of the frame is annealed.

21. A method of manufacturing a sheath, comprising:

extruding a nylon core;

braiding metal wires over the nylon core to form a frame;

heating and stretching the nylon core to reduce the diameter of the nylon core for removal of the frame;

annealing a plurality of distinct portions of the frame, wherein annealed portions of the frame are separated by unannealed portions of the frame;

reflowing a liner to an interior surface of the frame and a jacket to an exterior surface of the frame to form a composite conduit;

cutting the composite conduit at the annealed portions to form a plurality of sheath shafts such that the annealed portions are located at a distal end of each of the plurality of sheath shafts, the annealed portions being less than a length of each of the sheath shafts; and overmolding a hub around a proximal portion of the sheath shafts, wherein the sheath shaft is 7 French and comprises an inner diameter to outer diameter ratio between 0.92 and 0.93.

* * * * *